(12) United States Patent
Sakaguchi

(10) Patent No.: US 8,590,134 B2
(45) Date of Patent: Nov. 26, 2013

(54) MANUFACTURING METHOD FOR ABSORBENT PRODUCTS AND MANUFACTURING DEVICE FOR ABSORBENT PRODUCTS

(75) Inventor: Satoru Sakaguchi, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 329 days.

(21) Appl. No.: 12/935,601

(22) PCT Filed: Mar. 31, 2009

(86) PCT No.: PCT/JP2009/056619
§ 371 (c)(1),
(2), (4) Date: Feb. 7, 2011

(87) PCT Pub. No.: WO2009/123176
PCT Pub. Date: Oct. 8, 2009

(65) Prior Publication Data
US 2011/0173794 A1    Jul. 21, 2011

(30) Foreign Application Priority Data

Mar. 31, 2008  (JP) ................................. 2008-094066
Feb. 27, 2009  (JP) ................................. 2009-046786

(51) Int. Cl.
*B23P 21/00*  (2006.01)
*B29C 65/00*  (2006.01)

(52) U.S. Cl.
USPC ........................................... 29/469; 156/443

(58) Field of Classification Search
USPC ............ 29/428, 469, 419.1; 604/396, 385.01; 156/66, 443, 304, 216, 270, 247, 510
See application file for complete search history.

(56) References Cited

U.S. PATENT DOCUMENTS

| 7,214,285 | B2 * | 5/2007 | Guenther et al. ............. 156/204 |
| 2002/0138056 | A1 | 9/2002 | Kuen et al. |
| 2003/0135184 | A1 * | 7/2003 | Van Gompel et al. ... 604/385.01 |
| 2004/0188004 | A1 | 9/2004 | Guenther et al. |

FOREIGN PATENT DOCUMENTS

| EP | 1300123 A1 | 4/2003 |
| EP | 1452158 A1 | 9/2004 |
| EP | 1698313 A1 | 9/2006 |

(Continued)

OTHER PUBLICATIONS

International Search Report for PCT/JP2009/056619 mailed Jun. 30, 2009.

(Continued)

*Primary Examiner* — John C Hong
(74) *Attorney, Agent, or Firm* — Lowe Hauptman & Ham, LLP

(57) ABSTRACT

Provided is a manufacturing method for absorbent products that has a process for placing on connected rectangular flaps that are continuously conveyed on a flap line fastening members that are fastenable on both sides to prescribed areas near center line that is parallel to the MD-direction, a process for forming a cutable line along the center line that can divide the connected flaps in two, a process for forming flaps by cutting the connected flaps along the CD-direction on the flap line, and a process for placing the flaps on connected front torso-surrounding member or back torso-surrounding member or on the main body line so that center line is orthogonal to the MD-direction of the main body line.

9 Claims, 9 Drawing Sheets

(56) References Cited

FOREIGN PATENT DOCUMENTS

| | | |
|---|---|---|
| JP | 48049542 | 7/1973 |
| JP | 59165404 | 11/1984 |
| JP | 60-185606 U | 9/1985 |
| JP | 2004-524113 | 8/2004 |
| JP | 2005503892 | 2/2005 |
| JP | 2005-526530 A | 9/2005 |
| JP | 2005533529 | 11/2005 |
| JP | 2006340862 A | 12/2006 |
| WO | 8404242 A1 | 11/1984 |
| WO | 0226183 A1 | 4/2002 |
| WO | 03-028605 A1 | 4/2003 |

OTHER PUBLICATIONS

Office Action corresponding to CN 200980111904.9, dated Oct. 9, 2012.

Official Action as issued on Feb. 26, 2013 in counterpart Japanese Application.

Office Action issued on Aug. 12, 2013 corresponds to Australian patent application No. 2009232762.

Extended European Search Report issued on Sep. 6, 2013 corresponds to European patent application No. 09727668.7.

Official Action as issued on Mar. 27, 2013 in counterpart GC Patent Application No. 2009/13180.

\* cited by examiner

MANUFACTURING METHOD FOR ABSORBENT PRODUCTS AND MANUFACTURING DEVICE FOR ABSORBENT PRODUCTS

RELATED APPLICATIONS

The present application is a national phase of PCT/JP2009/056619, filed Mar. 31, 2009, and claims priority from, Japanese Application Numbers 2008-094066, filed Mar. 31, 2008, and 2009-046786, filed Feb. 27, 2009.

TECHNICAL FIELD

The present invention relates to a manufacturing method and a manufacturing apparatus for absorbent articles each of which includes: a front waistline member, a rear waistline member and a crotch member that connects the front waistline member and the rear waistline member.

BACKGROUND ART

In general, in order to be easily put on the wearer, an open-type diaper needs to be provided with: a vertically long absorber (absorber body) that absorbs body fluid from the body of the wearer, a diaper main body to which the absorber is attached, side flaps (hereinbelow referred to as flap) that project outwardly, in the width direction of the absorber from the absorber body.

Heretofore, as a manufacturing method for such open-type diaper provided with the flaps, following method has been known (For Example, Patent Literature 1)

(1) forming, on a continuum of flaps (continuous belt part), a potential cut line between each first belt part sheet fastener and each second belt part sheet fastener both placed in a direction (CD direction) crossing the moving direction (MD direction) of the continuum of flaps (flap continuum).

(2) placing the continuum of flaps (continuous belt part) along one edge portion of a continuum of the diaper main bodies (diaper main body continuum), and forming a bonding region in the CD direction.

Patent Literature 1: Japanese Patent Application Publication No. 2006-340862

However, in the above manufacturing method for an open-type diaper, the potential cut line is orthogonal to the MD direction of a flap line on which the continuum of flaps (continuous belt part) is transported. Accordingly, there has been a problem that, when the strength of the potential cut line is increased so as to prevent the flap continuum from being torn along the potential cut line on the flap line, a user of the manufactured diaper may find it difficult to tear along the potential cut line.

Further, in the above manufacturing method for the open-type diaper, the potential cut line is orthogonal to the MD direction of the flap line on which the flap continuum (continuous belt part) is transported. Accordingly, when the strength of the potential cut line is formed to be weak so as to be easily torn by a user, the potential cut line may be torn while the flap continuum is continuously transported on the flap line. Thus, there has been a problem that the flap continuum cannot be stably transported on the flap line, or a manufacturing facility for the diaper becomes complex since high level controls are required for continuously transporting the flap continuum.

Moreover, in the above manufacturing method for the open-type diaper, the flap continuum (continuous belt part) is placed along one edge portion of the diaper main body continuum so as to form the bonding region in the CD direction. Accordingly, there has been a problem that, when a user of the manufactured diaper unfolds and develops the flap, a force is applied on the bonding region in the direction of peeling the flap, and thereby the flap easily peels off from the diaper main body.

The present invention has been made in view of the above-described problems, and has an object of providing a manufacturing method and a manufacturing apparatus for absorbent articles being able to form a potential cut line along which a user can easily tear and to achieve the continuous transportation of the flap continuum (continuous belt part) on the flap line without using high level controls.

Another object of the present invention is to provide a manufacturing method and a manufacturing apparatus for absorbent articles being able to enhance a bonding strength in the bonding region formed between a flap continuum (continuous belt part) and a continuum of rear waistline members (one edge portion of a continuum of diaper main bodies).

DISCLOSURE OF THE INVENTION

An aspect of the present invention is summarized as a manufacturing method for absorbent articles including front waistline members, rear waistline members, and crotch members that connect the front waistline members and the rear waistline members. The manufacturing method for the absorbent articles includes: placing a latch member that can be attached to and locked in a predetermined region, on both sides of a vicinal region of a center line extending along a moving direction of a flap line, on a flap continuum having a long shape and being continuously transported on the flap line; forming a potential cut line that halves the flap continuum along the center line; forming the flaps on the flap line, by cutting the flap continuum in a direction orthogonal to the moving direction of the flap line; and placing, on a main body line, the flaps on a front waistline member continuum or on a rear waistline member continuum, so that the center line is orthogonal to a moving direction of the main body line.

As described above, the present invention can provide a manufacturing method and a manufacturing apparatus for absorbent articles being able to form a potential cut line along which a user can easily tear and to achieve a continuous transportation of a flap continuum (continuous belt part) on a flap line without using high level controls.

In addition, the present invention can provide a manufacturing method and a manufacturing apparatus for absorbent articles being able to enhance a bonding strength in the bonding region formed between a flap continuum (continuous belt part) and a continuum of rear waistline members (one edge portion of a continuum of diaper main bodies).

PREFERRED EMBODIMENTS FOR CARRYING OUT THE INVENTION

Hereinbelow, a first, a second, and other embodiments of the present invention will be described, by referring to the accompanying drawings.
[First Embodiment]

Figure 1:
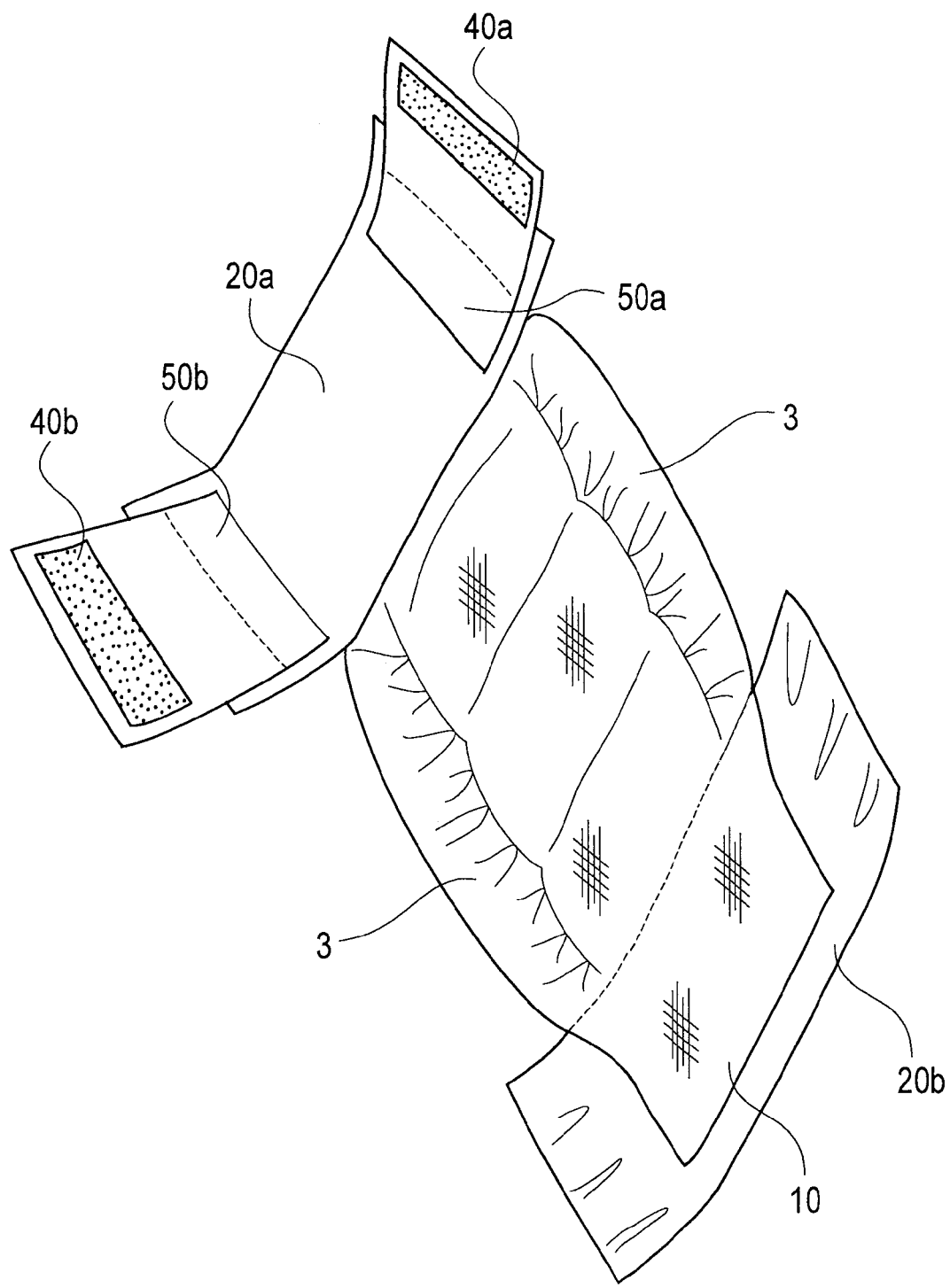
FIG. 1 is a perspective view showing an overall structure of an absorbent article according to a first embodiment of the present invention.
Figure 2:
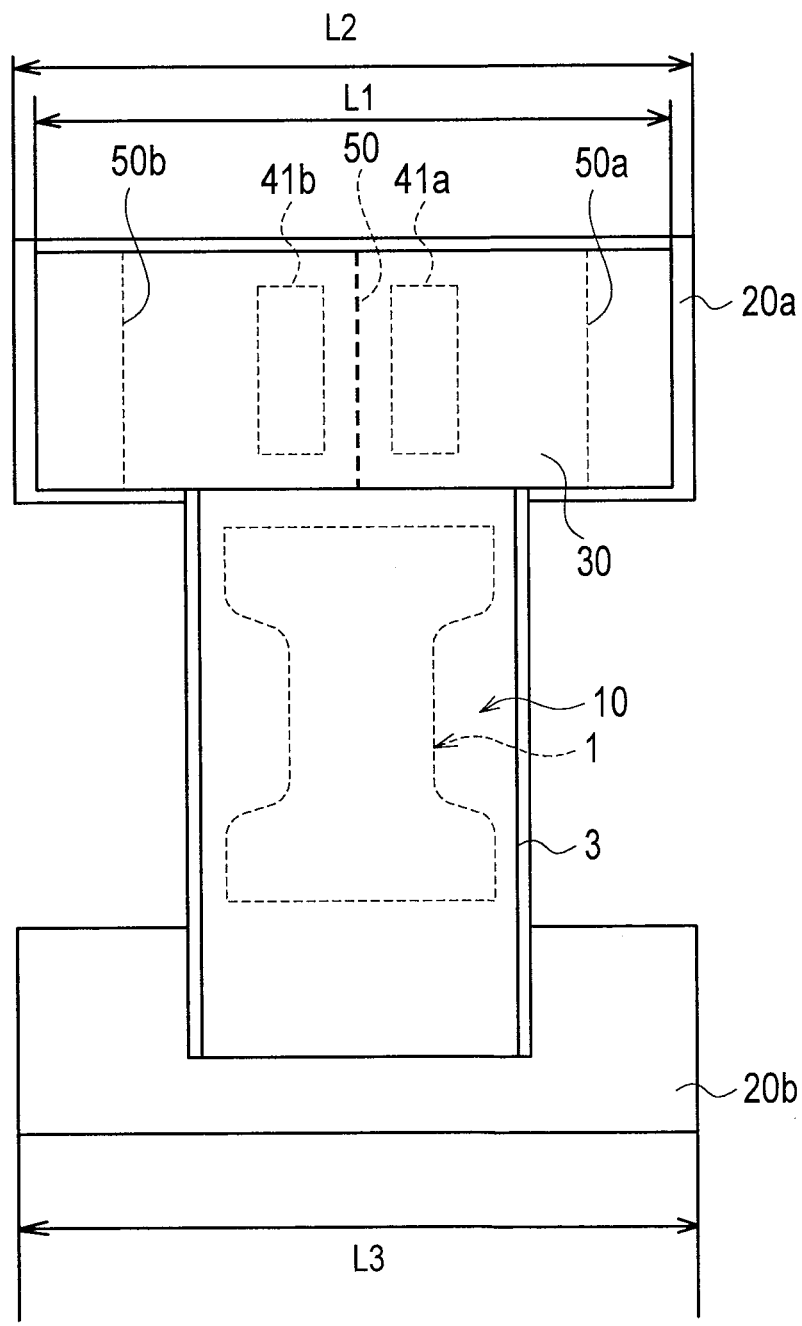
FIG. 2 is a plan view of an absorbent article according to the first embodiment of the present invention.
Figure 3:
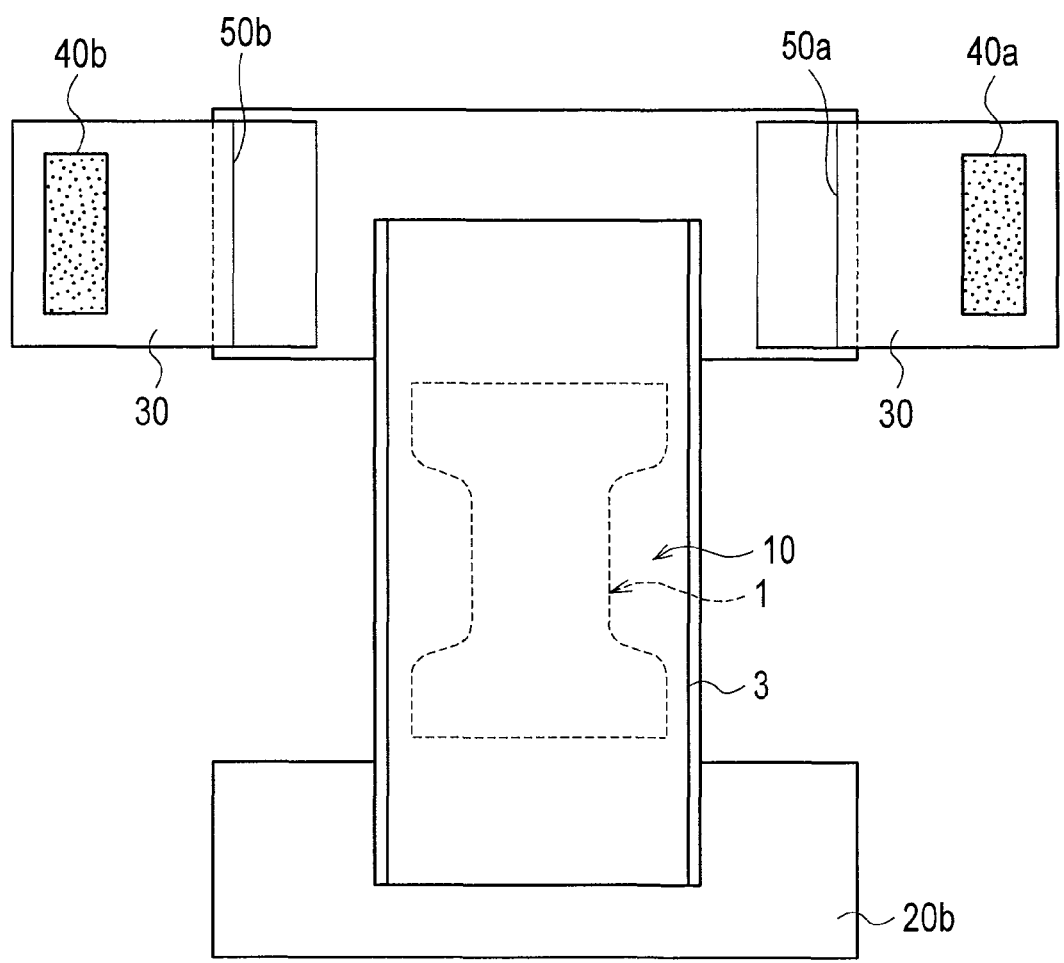
FIG. 3 is a plan view of a developed state of the absorbent article according to the first embodiment of the present invention.

First, a configuration of the absorbent article according to the first embodiment will be described by referring to the accompanying drawings. FIG. 1 is a perspective view showing an overall structure of an absorbent article according to a first embodiment of the present invention. FIG. 2 is a plan view of the closed state of an absorbent article according to the first embodiment of the present invention. FIG. 3 is a plan view of a developed state of the absorbent article according to the first embodiment of the present invention. The absorbent article described in the first embodiment relates to an open-type diaper manufactured by the manufacturing method for the absorbent article to be described later.

As shown in FIGS. 1 to 3, each of the absorbent articles is provided with a front waistline member 20b, a rear waistline member 20a, a crotch member (absorber body) 10, and a flap 30. The crotch member (absorber body) 10 connects the front waistline member 20b and the rear waistline member 20a. The flap 30 is placed on the rear waistline member 20a.

As shown in FIGS. 2 and 3, latch members 40a and 40b are locked on and temperately bonded to a rear waistline member 20a. The flap 30 is provided with the potential cut line (perforated line) 50 to be torn off by the user of the manufactured diaper.

Figure 4:
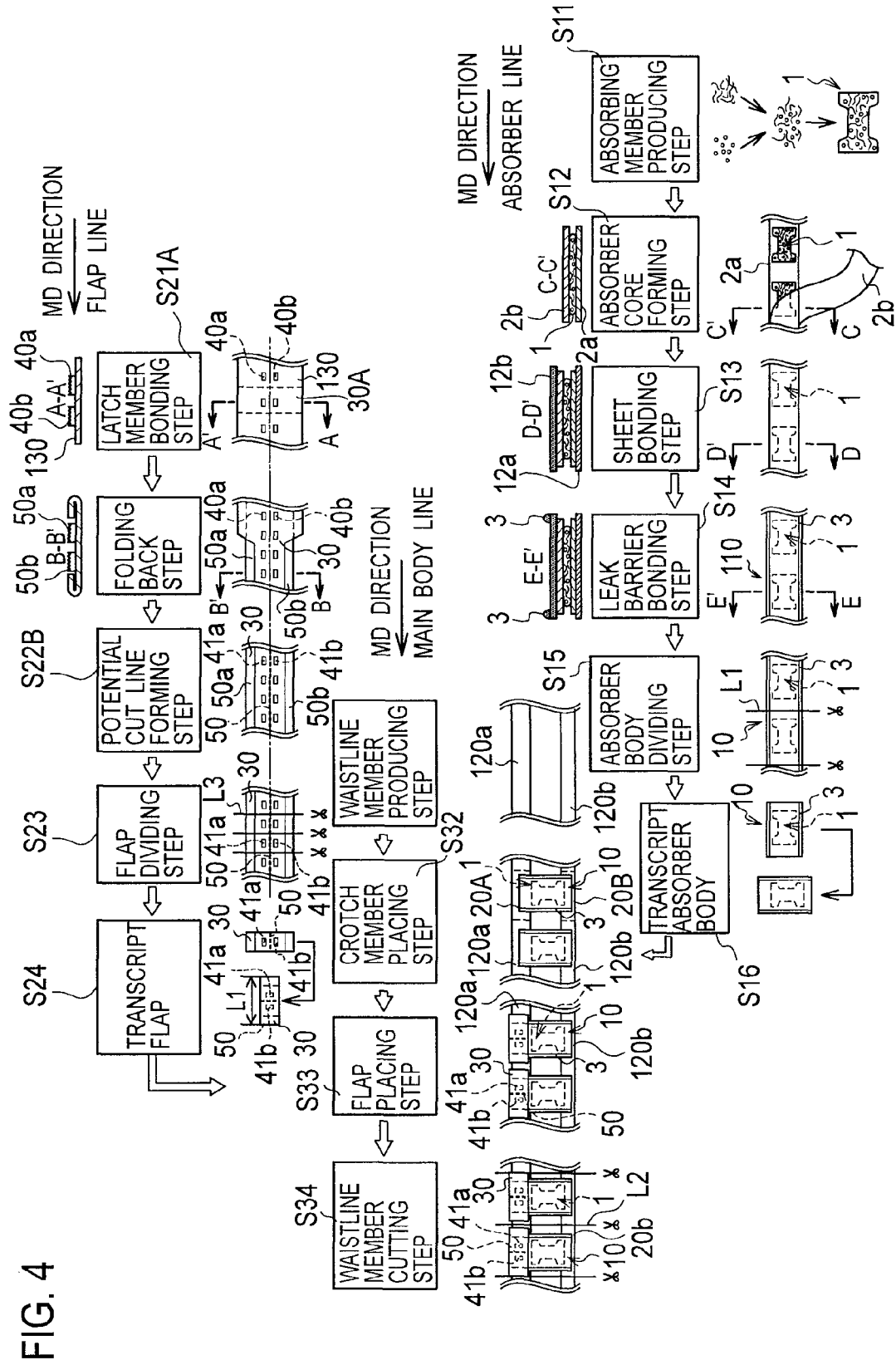
FIG. 4 is a diagram for illustrating a manufacturing method for an absorbent article according to the first embodiment of the present invention.

Subsequently, by referring to the accompanying drawings, description will be given of a manufacturing method for the absorbent articles according to the first embodiment. FIG. 4 is a diagram for illustrating a manufacturing method for absorbent articles according to the first embodiment of the present invention.

The manufacturing method for the absorbent articles includes: steps performed on an absorber line, steps performed on a flap line, and steps performed on a main body line.

Firstly, steps performed on the absorber line, on which the absorbers placed on the crotch members 10 are transported, will be described.

In step S11, a crusher crushes a pulp sheet to produce crushed pulp. Then, when the crushed pulps pass through a pulp supply duct, super absorbent polymer (SAP) is mixed thereto. Then, the mixture of the crushed pulp and the super absorbent polymer, which is supplied from the pulp supply duct, is layered in a predetermined shape by use of a layer drum, thereby absorber cores 1 (absorbers) are formed.

In step S12, on each of sheet tissues 2a that is continuously transported in the moving direction (hereinafter referred to as MD direction) of the absorber line, each of the absorber cores 1 is placed by a predetermined interval length in the MD direction of the absorber line. Subsequently, sheet tissues 2b being continuously transported in the MD direction of the absorber line are layered on the sheet tissues 2a, respectively. Here, along the MD direction of the absorber line, each of the absorber cores 1 is placed on each of the sheet tissues 2a.

In step S13, top sheets 12b (liquid permeable) being continuously transported in the MD direction of the absorber line are placed on and bonded with the sheet tissues 2b, respectively. In addition, back sheets 12a (liquid impermeable) being continuously transported in the MD direction of the absorber line are placed under and bonded with the sheet tissues 2a, respectively.

In step S14, leak barriers 3 each formed of different members are respectively bonded onto both side edges of the absorber bodies 10 in the MD direction of the absorber line.

In step S15, the continuum of the crotch members (the crotch member continuum 110) (absorber body) being continuously transported in the MD direction of the absorber line is transported by use of a rotation of a rotating drum. Concurrently, the crotch member continuum 110 is cut along the crossing direction to the MD direction (hereinafter referred to as CD direction), by a predetermined interval length by use of a cutter roll arranged opposite to the outer peripheral surface of the rotating drum.

In step S16, each of the crotch members 10 (absorber bodies) formed by the above-described step S15 is placed between the front waistline member continuum 120b and the rear waistline member continuum 120a, so that the center line C of the absorber line is orthogonal to the MD direction of the main body line. In other words, each of the crotch members 10 is rotated by 90° and is inverted vertically. Thereafter, each of the crotch members 10 is bonded to the space between the front waistline member continuum 120b and the rear waistline member continuum 120a by use of a thermoplastic resin.

Secondly, steps performed on the flap line, on which the flaps 30 to be placed on the rear waistline member 20a are transported, will be described.

In step S21A, by use of a latch member placing structure 210 to be described later, on the flap continuum 130 having a long shape and being continuously transported on the flap line, latch members 40a and 40b that can be attached to and locked in a predetermined region of the front waistline members 20b are placed on both sides of the center line C that extends along the MD direction of the flap line.

Specifically, the latch members 40a and 40b are placed on the continuum of the flaps (the flap continuum 130) by a predetermined interval length, on both sides of a vicinal region of the center line C that extends along the MD direction of the flap line.

In this regard, one latch member may be placed across both sides of the center line C instead of placing the two latch members 40a and 40b on both sides of the center line C.

In step S22A, on the flap line, by use of an edge portion folding back structure 220 to be described later, the side edge portions 50a and 50b placed on both sides of the flap continuum 130 are folded back toward the center line C side. Specifically, as shown in the cross-sectional view taken along B-B' line, on the flap line, both of the side edge portions 50a and 50b of the flap continuum 130 are folded back toward the upper side of the flap continuum 130.

In this regard, both of the side edge portions 50a and 50b of the flap continuum 130 may be folded back several times on the flap line. Further, in order to prevent the flap continuum 130 from being turned over while being transported, an embossing step or the like may be performed on folded back portions 51a and 51b, which is formed by folding back both of the side edge portions 50a and 50b, to be temporarily bonded onto the flap continuum 130. Here, the folded back portions 51a and 51b are referred to as portions formed by the side edge portions 50a and 50b being folded back to cause the flap continuum 130 to overlap.

In step S22B, by use of a cut line forming structure 230 to be described later, on the flap continuum 130, a potential cut line (perforated line) 50 that halves the flap continuum 130 is formed.

Note that, the potential cut line 50 may be formed in steps S21A, S22A or S23. In addition, the potential cut line 50 may be straight or curved as long as it extends along the center line C.

In step S23, on the flap line, by use of a continuum cutting roll 241 of a cutting and rotating structure 240 to be described later, the flap continuum 130 is cut by the predetermined interval length, in the CD direction of the flap line. Thereby, each of the flaps 30 is formed.

Here, in any one of the steps performed on the flap line, a cut-out portion (not shown) having a predetermined shape (for example, curved-shape along a leg) may be formed in a part of the vicinal region of the center line C.

In step S24, on the flap line, by use of a rotating drum 242 of a cutting and rotating structure 240 to be described later, the flaps 30 each formed in step S23 is rotated by 90° and is inverted vertically. Thereafter, each of the flaps 30 is bonded onto the rear waistline member continuum 120a by use of a thermoplastic resin.

Thirdly, steps performed on the main body line, on which the front waistline member continuum 120b and the rear waistline member continuum 120a are transported, will be described.

In step S31, a pair of continuums of waistline members (the front waistline member continuum 120b and the rear waistline member continuum 120a) having a long shape is formed of a non-woven fabric is transported in the MD direction of the main body line. Note that, the front waistline member continuum 120b and the rear waistline member continuum 120a may have stretching properties.

In step S32, each of the crotch members 10 formed in step S15 on the absorber line is placed while being spaced apart from one another, in the MD direction of the main body line, between the front waistline member continuum 120b and the rear waistline member continuum 120a, both having long shapes and being continuously transported on the main body line. In other words, on the flap line, each of the crotch members 10 is rotated by 90° and is inverted vertically. Thereafter, by use of a thermoplastic resin, each of the crotch members 10 is bonded to the space between the front waistline member continuum 120b and the rear waistline member continuum 120a both having long shapes.

In step S33, on the main body line, the flap 30 formed in the above-described step S23 is placed on the rear waistline member continuum 120a so that the center line C of the flap 30 is orthogonal to the MD direction of the main body line. In other words, on the flap line, the flaps 30 each formed in step S23 is rotated by 90° and is inverted vertically. Thereafter, each of the flaps 30 is bonded onto the rear waistline member continuum 120a by use of a thermoplastic resin.

Specifically, in step S33, on the main body line, each of the flaps 30 is bonded onto the rear waistline member continuum 120a so that each of the flaps 30 is respectively placed on the region 20A constituting each of the absorbent articles (rear waistline members 20a) from the rear waistline member continuum 120a.

In this regard, in step S33, it is preferable that the flaps 30 be bonded onto the rear waistline member continuum 120a by use of a thermo compression or the like, using an embossing roller or ultrasonic waves. Furthermore, the thermoplastic resin may be applied onto the entire back surface side of the flaps 30, the entire back surface corresponding to the folded back portions 51a and 51b. Alternatively, the thermoplastic resin may be applied onto only a part of the back surface side of the flaps 30, the part of the back surface corresponding to the folded back portions 51a and 51b.

When the side edge portions 50a and 50b of the flap continuum 130 are folded back several times on the flap line, a thermoplastic resin coating is applied to at least part of a surface that contacts the rear waistline member continuum 120a.

In step S34, on the main body line, the front waistline member continuum 120b and the rear waistline member continuum 120a are cut in the CD direction of the main body line by a predetermined interval length.

Specifically, the front waistline member continuum 120b and the rear waistline member continuum 120a are cut so that a length L3 of each of the front waistline members 20b in the width direction of the absorbent articles and a length L2 of each of the rear waistline members 20a in the width direction of the absorbent articles can be equal.

Here, the width L1 in the direction crossing the center line C of each of the flaps 30 is shorter than a predetermined length (pitch) L2 that is the cut length of the front waistline member continuum 120b and the rear waistline member continuum 120a.

Note that, prior to the step S34, a step of attaching the front waistline member continuum 120b and the rear waistline member continuum 120a, in other words, a step of folding back the crotch members 10 on the center line C, may be additionally performed. In that case, after each of the crotch members 10 is folded back on the center line C, in the above-described step S 34, the front waistline member continuum 120b and the rear waistline member continuum 120a are cut.

Hereinbelow, a manufacturing apparatus for absorbent articles according to the first embodiment will be described by referring to the accompanying drawings. FIGS. 5 to 8 are drawings for explaining the manufacturing apparatus for the absorbent articles according to the first embodiment.

The manufacturing apparatus for the absorbent articles is provided with: a latch member placing structure 210; an edge portion folding back structure 220; a potential cut line forming structure 230; and a cutting and rotating structure 240 (a cutting and placing structure).

Figure 5:
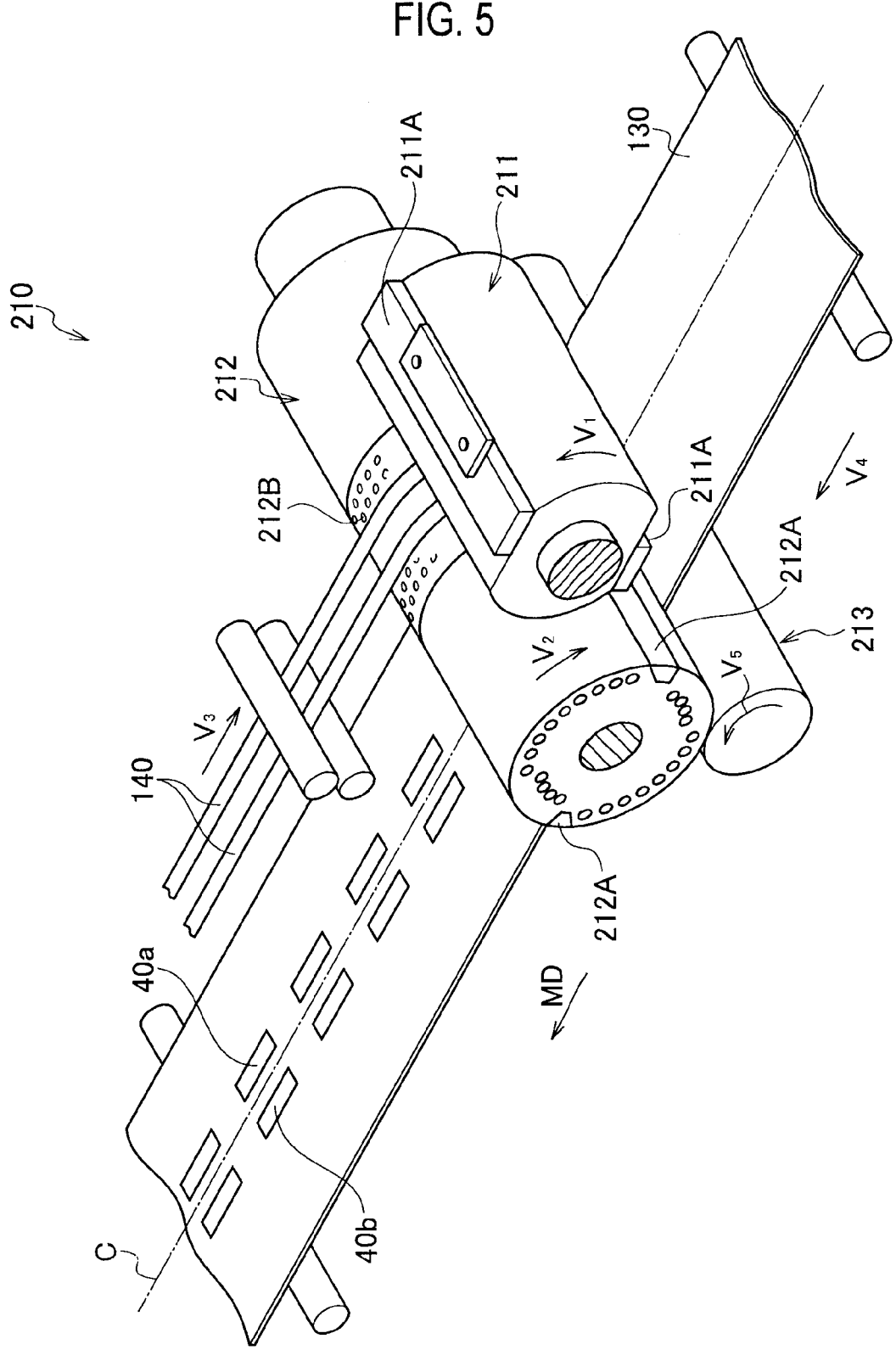
FIG. 5 is a perspective view of a latch member placing structure 210 according to the first embodiment of the present invention.

First, the latch member placing structure 210 according to the first embodiment will be described by referring to the accompanying drawings. FIG. 5 is a perspective view of the latch member placing structure 210 according to the first embodiment of the present invention.

As shown in FIG. 5, as described in the above step S21A, the latch member placing structure 210 places the latch members 40a and 40b by a predetermined interval length, on both sides of the vicinal region of the center line C that extends along the MD direction of the flap line.

Specifically, the latch member placing structure 210 is mainly provided with: an upper blade roll 211, a lower blade roll 212, and a transcript roll 213. Note that, the upper blade roll 211, the lower blade roll 212, and the transcript roll 213 are configured to rotate by using a shaft (not shown) as a center, respectively.

The upper blade roll 211 includes two blades 211A for cutting the latch member continuum 140. The circumferential velocity ($V_1$) of the upper blade roll 211 is substantially same as the circumferential velocity ($V_2$) of the lower blade roll 212.

In addition, the circumferential velocity ($V_1$) of the upper blade roll 211 is faster than the feeding velocity ($V_3$) in which the driving roll (not shown) feeds the latch member continuum 140 to the lower blade roll 212. The circumferential velocity ($V_1$) of the upper blade roll 211 is substantially same as or slower than the moving velocity ($V_4$) of the flap continuum 130 that is continuously transported by the driving roll (not shown).

The lower blade roll 212 includes two stationary blades 212A that contacts with the blade 211A so as to cut the latch member continuum 140. The lower blade roll 212 is provided with a plurality of suction holes 212B configured to suck the latch member continuum 140. The lower blade roll 212 rotates in a direction opposite to that of the upper blade roll 211. As described above, the circumferential velocity ($V_2$) of the lower blade roll 212 is substantially same as the circumferential velocity ($V_1$) of the upper blade roll 211.

Between the lower blade roll 212 and the transcript roll 213, the transcript roll 213 transcripts (attaches), on the flap continuum 130, the latch members 40a and 40b cut by the upper blade roll 211 and the lower blade roll 212.

The circumferential velocity ($V_5$) of the transcript roll 213 is substantially same as the moving velocity ($V_4$) of the flap continuum 130. In other words, the circumferential velocity ($V_5$) of the transcript roll 213 is substantially same as or faster than the circumferential velocity ($V_2$) of the lower blade roll 212 and the circumferential velocity ($V_1$) of the upper blade roll 211.

Figure 6:
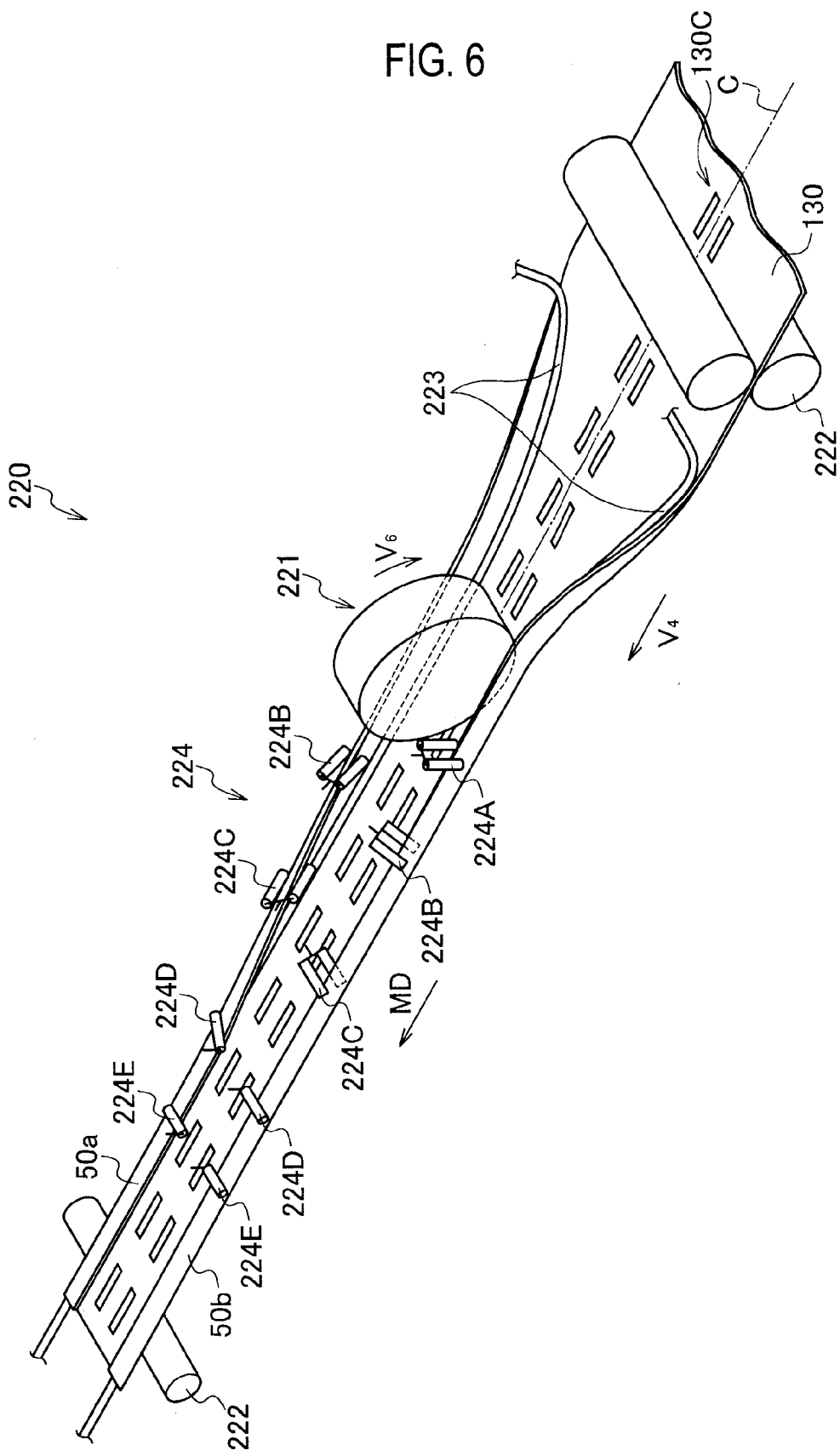
FIG. 6 is a perspective view of an edge portion folding back structure 220 according to the first embodiment of the present invention.

Next, the edge portion folding back structure 220 according to the first embodiment will be described by referring to the accompanying drawings. FIG. 6 is a perspective view of the edge portion folding back structure 220 according to the first embodiment of the present invention.

As shown in FIG. 6, as described in the above step S22A, the side edge portions 50a and 50b placed on both sides of the flap continuum 130 are folded back toward the center line C side.

Specifically, the edge portion folding back structure 220 is mainly provided with: a large diameter roll 221, a transporting roll 222, a folding center bar 223, and a guiding roll 224. Note that, the large diameter roll 221, the transporting roll 222, the folding center bar 223, and the guiding roll 224 are configured to rotate by using a shaft (not shown) as a center, respectively.

The large diameter roll 221 contacts with the center region 130C of the flap continuum 130 (that is, center line C side with respect to the side edge portions 50a and 50b), and cause, along with the guiding roll 224 to be described later, the side edge portions 50a and 50b to stand.

The transporting roll 222 transports the flap continuum 130 in a substantially horizontal state. In other words, the flap continuum 130 is transported in a substantially horizontal state by the transporting roll 222.

The folding center bar 223 holds the folding back position, when the side edge portions 50a and 50b are folded back. The folding center bar 223 extends in the MD direction, and is placed in substantially parallel with the flap continuum 130 that is transported by the transporting roll 222.

The guiding roll 224 guides the side edge portions 50a and 50b so as to fold back the side edge portions 50a and 50b toward the center line C side. The guiding roll 224 is provided with a plurality of guiding rolls 224A to 224E.

The side edge portions 50a and 50b are caused to stand and to be folded back via the folding center bar 223, gradually from the vicinity of the guiding roll 224A to the vicinity of the guiding roll 224E. In other words, the inclined angle of the side edge portions 50a and 50b with respect to the center region 130C of the flap continuum 130 becomes gradually small, from the vicinity of the guiding roll 224A to the vicinity of the guiding roll 224E.

In this regard, in order to prevent the flap continuum 130 from being turned over while being transported, after the side edge portions 50a and 50b are folded back, an embossing step or the like may be performed on the folded back portions so that the side edge portions 50a and 50b are temporarily bonded to the flap continuum 130. Here, the folded portions are referred to as portions formed by the side edge portions 50a and 50b being folded back to cause the flap continuum 130 to overlap.

Figure 7:
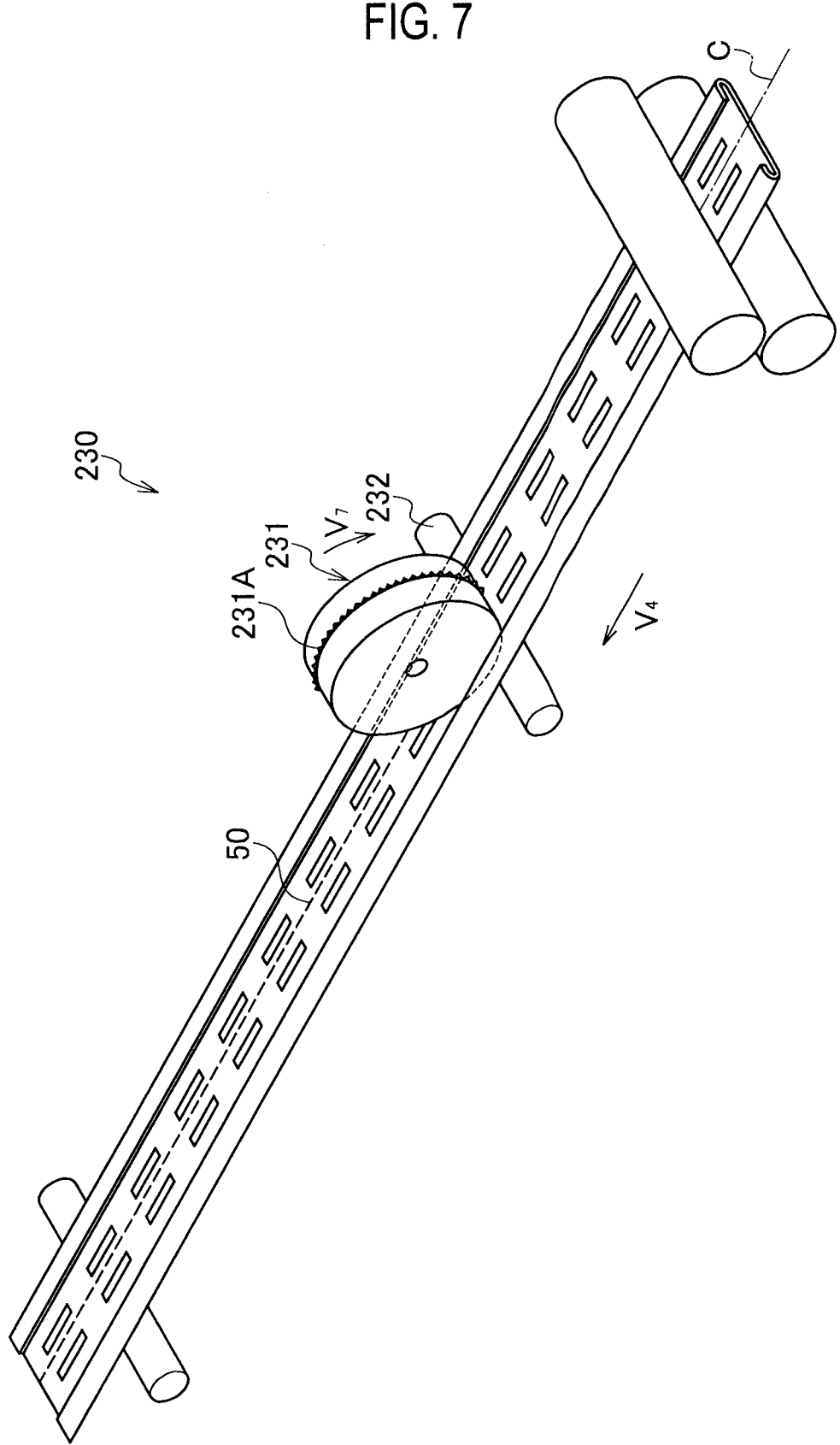
FIG. 7 is a perspective view of a potential cut line forming structure 230 according to the first embodiment of the present invention.

Next, the potential cut line forming structure 230 according to the first embodiment will be described by referring to the accompanying drawings. FIG. 7 is a perspective view of the potential cut line forming structure 230 according to the first embodiment of the present invention.

As shown in FIG. 7, as described in the above step S22B, on the flap continuum 130, a potential cut line (perforated line) 50 that halves the flap continuum 130 along the center line in the MD direction of the flap line is formed. Here, the potential cut line 50 may be straight or curved as long as it extends along the center line C.

The potential cut line forming structure 230 is provided with: a cutting roll 231 configured to rotate by using a shaft (not shown) as a center; and a nipping roll 232 configured to nip the flap continuum 130 between the cutting roll 231 and the nipping roll 232.

The circumferential velocity ($V_7$) of the cutting roll 231 is substantially same as the moving velocity ($V_4$) of the flap continuum 130. The cutting roll 231 includes a cutting process protrusion 231A for forming the potential cut line along the center line C.

Figure 8:
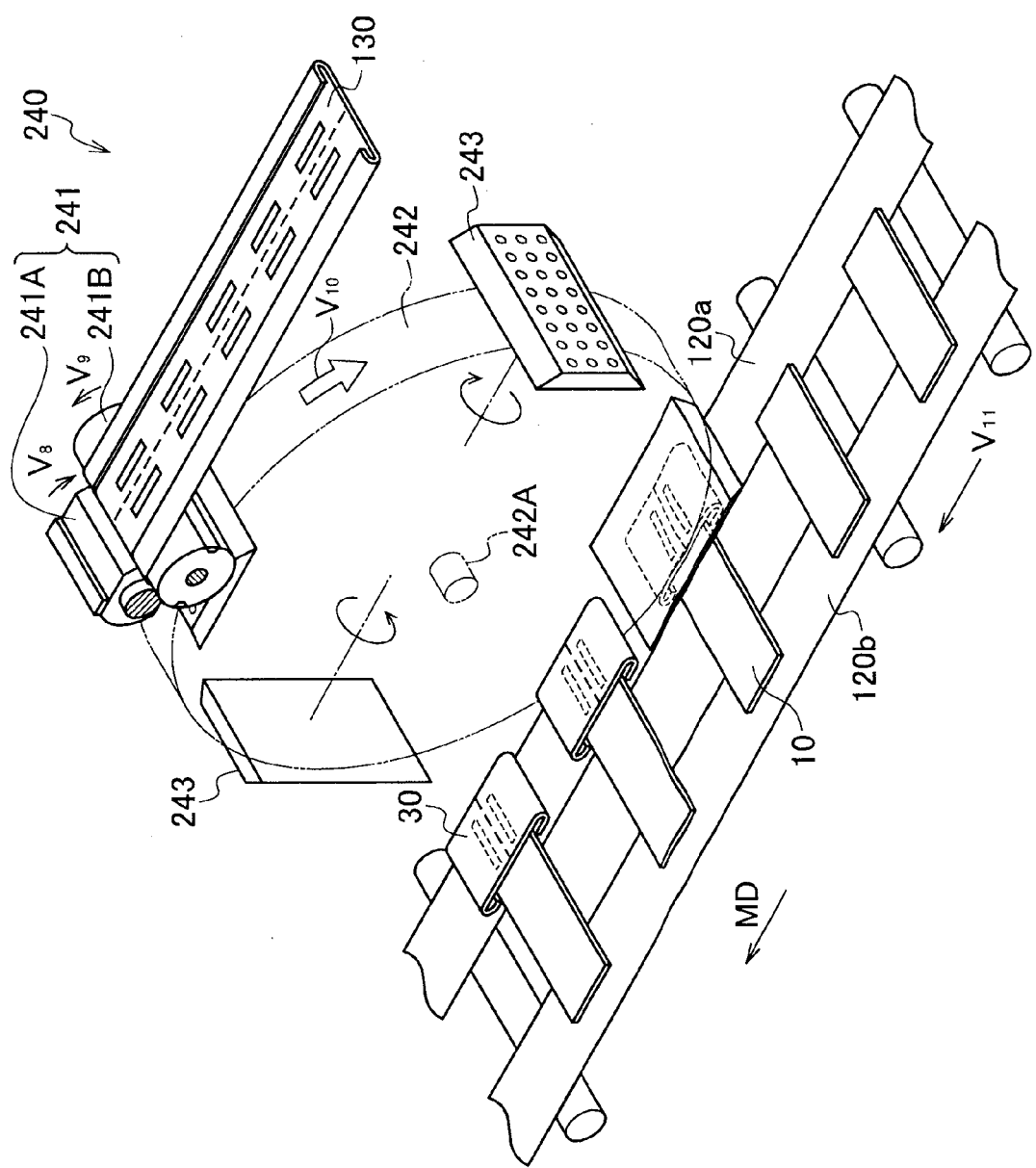
FIG. 8 is a perspective view of a cutting and rotating structure 240 according to the first embodiment of the present invention.

Next, a cutting and rotating structure 240 will be described by referring to accompanying drawings. FIG. 8 is a perspective view of the cutting and rotating structure 240 according to the first embodiment of the present invention.

As shown in FIG. 8, as described in the above step S23, the cutting and rotating structure 240 forms each of the flaps 30 by cutting the flap continuum 130, by the predetermined interval length in the CD direction. Further, as described in the above step S24, each of the flaps 30 thus cut and formed is rotated by 90° and is inverted vertically by the cutting and rotating structure 240. Thereafter, the cutting and rotating structure 240 places each of the flap 30 on the rear waistline member continuum 120a.

Specifically, the cutting and rotating structure 240 is mainly provided with: a continuum cutting roll 241 and a rotating drum 242. The continuum cutting roll 241 is provided with: a blade roll having a blade (not shown); and a stationary blade 241B having a stationary blade (not shown). Note that, the circumferential velocity ($V_8$) of blade roll 241A is substantially same as the circumferential velocity ($V_9$) of the stationary blade 241B.

The rotating drum 242 includes a plurality of suction pads 243 configured to suck the flaps 30 cut by the blade roll 241A and the stationary blade roll 241B. The rotating drum 242 is configured to rotate by using the shaft 242A as a center so as to place the flaps 30, which are sucked by and attached to the suction pads 243, on the rear waistline member continuum 120a. Note that, the circumferential velocity ($V_{10}$) of rotating drum 242 is substantially same as the moving velocities ($V_{11}$) of the rear waistline member continuum 120a and the front waistline member continuum 120b.

While transporting the suction pads 243 to the upper side of the rear waistline member continuum 120a, the rotating drum 242 rotates the suction pads 243 by 90° by use of the rotating structure (not shown). In this manner, each of the flaps 30 is rotated by 90° and is inverted vertically by the cutting and rotating structure 240, and is bonded onto the rear waistline member continuum 120a.

According to the manufacturing method for the absorbent articles of the first embodiment of the present invention, it is possible to form the potential cut line 50 along which the users can easily tear, while achieving a continuous transportation of the flap continuum 130 on the flap line without using high level controls.

Specifically, in the manufacturing method for the absorbent articles according to the first embodiment of the present invention, a potential cut line is formed to extend in a moving direction of the flap line. Accordingly, it is possible to maintain the strength of the potential cut line 50, and to prevent the potential cut line 50 from being torn while the flap continuum 130 is continuously transported on the flap line. Thereby, the flap continuum 130 can be stably transported. Additionally, high level controls are not required for continuously transporting the flap continuum 130 so that a complex manufacturing facility for the diaper is not required.

In the manufacturing method for the absorbent articles' according to the first embodiment of the present invention, the bonding regions for bonding the flaps 30 with the rear waistline member continuum 120a is formed on both of the folded back portions 51a and 51b of the flaps 30 (on the back surface of the flaps 30).

Accordingly, when such flaps are unfolded and developed, forces are applied on the shear direction of the bonding region. Accordingly, the bonding strength in the bonding region can be enhanced and thus eliminates the need for a step of complementing bonding strength in the bonding region.

In addition, when the embossing process or the like is performed on both of the side edge portions 50a and 50b of the flaps 30 so as to be temporarily bonded, the flap continuum 130 can be prevented from being turned over while being transported. Further, after each of the flaps 30 is bonded onto the rear waistline member continuum 120a on the main body line, the flaps 30 can be prevented from being folded back while being transported on the main body line.

According to the manufacturing method for the absorbent articles according to the first embodiment of the present invention, each members (for example, the crotch members 10) can be continuously transported on the main body line. Therefore, a stable transportation can be realized and the absorbent articles can be manufactured without requiring any complex step.

According to the manufacturing method for the absorbent articles of the first embodiment of the present invention, the width L1 in the direction crossing the center line C of the flaps 30 is shorter than the predetermined length (pitch) L2. Accordingly, both of the side edge portions 50a and 50b of the flaps 30 can be prevented from being cut caused by the misalignment in the cutting process on the main body line.

According to the manufacturing method for the absorbent articles of the first embodiment of the present invention, the front waistline member continuum 120b and the rear waistline member continuum 120a are continuously transported. Accordingly, the edge portion of the front waistline member continuum 120b and the edge portion of the rear waistline member continuum 120a can be easily folded back and stacked. Therefore, the front waistline member continuum 120b and the rear waistline member continuum 120a thus stacked can be simultaneously cut. Thus, open-type diapers and pants-type diapers can be manufactured by the same cutting step. Therefore, the open-type diapers and the pants-type diapers can be manufactured without changing the cutting step or a cutter themselves.

According to the manufacturing method for absorbent articles of the first embodiment of the present invention, absorbent articles each having a pair of side flaps protruded from the absorber body can be manufactured without limitation in their product form.

[Second Embodiment]

Figure 9:
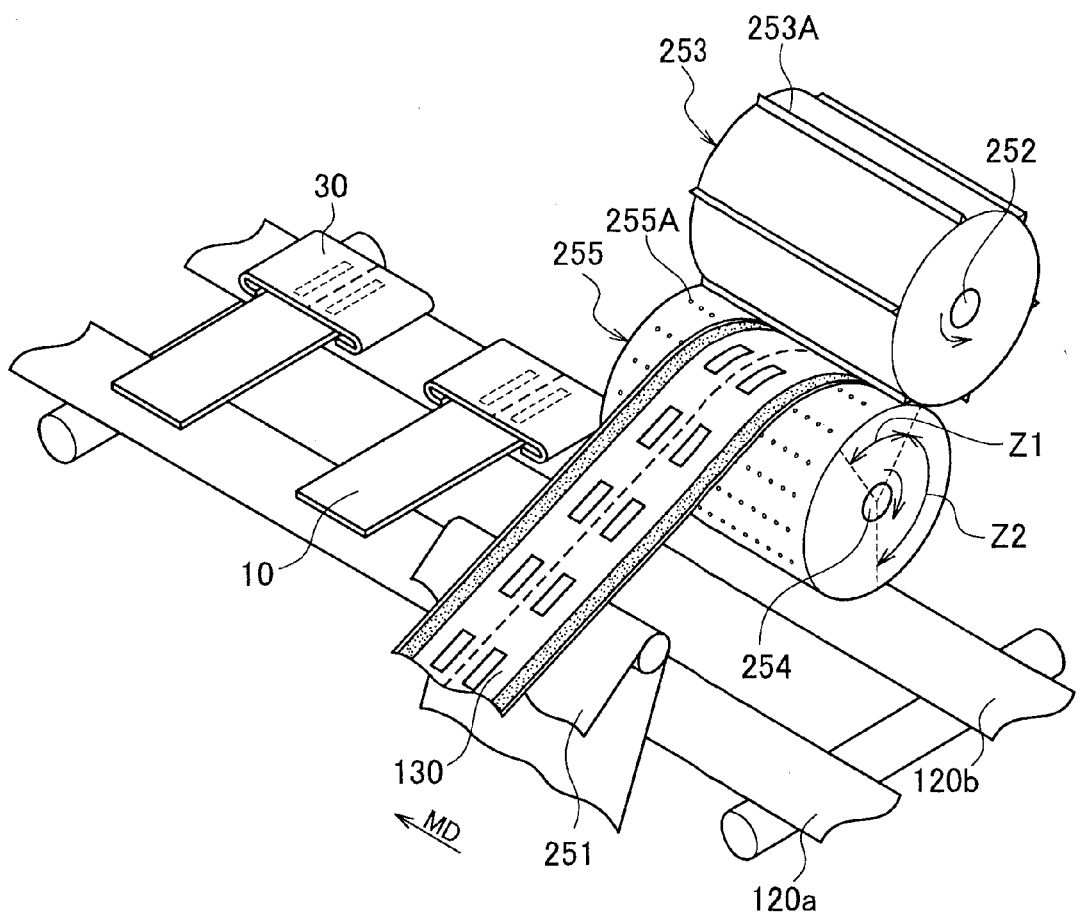
FIG. 9 is a perspective view of a cutting and placing structure 250 according to a second embodiment of the present invention.

Hereinbelow, a cutting and placing structure 250 according to the second embodiment will be described by referring to the accompanying drawings. FIG. 9 is a perspective view of the cutting and placing structure 250 according to the second embodiment of the present invention. Note that components having the same functions as the cutting and placing structure 250 of the first embodiment will be denoted by the same reference numerals, and descriptions will be mainly given for those different from the first embodiment.

Here, in the manufacturing method for the absorbent articles according to the present invention, each of the flaps 30 is placed on the rear waistline member continuum 120a so that the center line C is orthogonal to the MD direction of the main body line. In the above-described first embodiment, each of the flaps 30 is rotated by 90° and is inverted vertically, thereafter, each of the flaps 30 is bonded onto the rear waistline member continuum 120a. On the other hand, in the second embodiment, each of the flap 30 is bonded onto the rear waistline member continuum 120a, without being rotated by 90° and is inverted vertically.

The flap line is placed along the CD direction of the main body line (see FIG. 9). In other words, each of the flaps 30 is placed on the rear waistline member continuum 120a so that the center line C of the flaps 30 is orthogonal to the MD direction of the main body line. (Steps S24 and S 33)

The manufacturing apparatus for the absorbent articles according to the second embodiment includes the cutting and placing structure 250 instead of the cutting and rotating structure 240 described in the first embodiment. The structures other than the cutting and rotating structure 240 (i.e., the latch member placing structure 210, the edge portion folding back structure 220, and the potential cut line forming structure 230) is same as in the case of the first embodiment.

As shown in FIG. 9, the cutting and placing structure 250 cuts the flap continuum 130 by a predetermined interval length so as to form the flaps 30. Further, the cutting and placing structure 250 places each of the flaps 30 on the rear waistline member continuum 120a by use of a thermoplastic resin, without rotating each the flaps 30 formed by the cutting as described above.

Specifically, the cutting and placing structure 250 cuts the flap continuum 130, which is transported by an endless belt 251, by a predetermined interval length. Concurrently, the cutting and placing structure 250 attaches each of the flaps 30, which is formed by cutting the flap continuum 130, on the rear waistline member continuum 120a by use of a thermoplastic resin or the like.

The cutting and placing structure 250 is provided with: an upper blade roll 253 configured to rotate by using a shaft center 252 as a center; and a lower blade roll 255 configured to rotate by using a shaft center 254 as a center.

The upper blade roll 253 is provided with a plurality of blades 253A placed by a predetermined interval length on the outer peripheral surface thereof. Here, the plurality of blades 253A is placed in substantially parallel with the shaft center 252. The lower blade roll 255 is provided with: suction holes 255A configured to suck the flaps 30 formed by cutting the flap continuum 130; and a stationary blade (not shown) configured to cut the flap continuum 130 with the blade 253A.

The peripheral surface of the lower blade roll 255 is provided with: a first zone Z1 that sucks and holds the flap continuum 130 with a predetermined suction force; and a second zone Z2 that sucks and holds the flaps 30 formed by cutting the flap continuum 130 with a suction force stronger than that of the first zone Z1.

When the flap continuum 130 passes through the first zone Z1, while slipping around the peripheral surface of the lower blade roll 255, the flap continuum 130 is sucked by the suction holes 255A formed on the first zone Z1 so as to be held by the peripheral surface of the lower blade roll 255. At this time, the flap continuum 130 is cut between the blade 253A and the stationary blade. Thereby, each of the flaps 30 is formed.

When each of the flaps 30 passes through the second zone Z2, without slipping around the peripheral surface of the lower blade roll 255, the flap 30 is sucked by the suction hole 255A formed on the second zone Z2 so as to be held by the peripheral surface of the lower blade roll 255. Then, each of the flaps 30 approaches the rear front waistline member continuum 120a by the rotation of the lower blade roll 255A so as to be attached thereon.

As described above, according to the cutting and placing structure 250 of the second embodiment, same operations and effects can be obtained as in the case of the above-described first embodiment. In particular, the configuration of the cutting and placing structure 250 in which each of the flap 30 is rotated by 90° and is inverted vertically is not complex compared to the configuration of the cutting and rotating structure 240. Therefore, cost for manufacturing facility can be reduced.

[Other Embodiments]

The embodiments according to the present invention can be changed in the following manner, for example. Specifically, in the above-described embodiments, an explanation is given for an example in which the flaps 30, on which the latch members 40a and 40b that can be attached to and locked in the predetermined regions of the front waistline member 20b, are placed on the rear waistline member continuum 120a. However, the present invention is not limited to this example. In other words, the present invention is applicable to an example in which the flaps 30, on which the latch members 40a and 40b that can be attached to and locked in the predetermined regions of the rear waistline member 20a, is placed on the front waistline member continuum 120b.

It is a matter of course that orders of performing the steps in the above-described manufacturing method for the absorbent article is not limited to those described above as long as the absorbent article can be manufactured, and the steps to be performed can be appropriately selected in accordance with the intended purpose.

Diapers manufactured by the manufacturing method for absorbent articles according to the first embodiment of the present invention can be used as a tape-type diaper when torn along the potential cut line (perforated line) so that the flaps 30 are unfolded, and used as pad-type diapers when not torn along the perforated line. Accordingly, diapers manufactured by this method can be used as any of these two types in accordance with the intended use of the user.

As described above, the present invention has been described in detail by using the above-described embodiments. However, it is obvious for a person skilled in the art that the present invention is not limited to the embodiments described in this specification. The present invention can be implemented as a modification and an amended embodiment without departing from the content and scope of the present invention which is defined by the description of the scope of claims. Accordingly, the description of the present invention is intended to give description as an example and does not have any meaning to limit the present invention.

This application is based upon and claims the benefit of priority from the prior Japanese Patent Application No. JP 2008-094066, filed on Mar. 31, 2008, and the prior Japanese Patent Application No. JP 2009-046786, filed on Feb. 27, 2009; the entire contents of which are incorporated herein by reference.

Industrial Applicability

As described above, according to a manufacturing method for absorbent articles of the present invention, there can be provided a manufacturing method to enhance a bonding strength in the bonding region formed between a flap continuum (continuous belt part) and a continuum of rear waistline members (one edge portion of a continuum of diaper main bodies).

The invention claimed is:

1. A method of manufacturing absorbent articles including: a front waistline member, a rear waistline member, and a crotch member connecting the front waistline member and the rear waistline member, said method comprising:
continuously transporting an elongated flap continuum in a moving direction of a flap line, the flap continuum having a center line extending along the moving direction of the flap line;
placing latch members on both sides of a vicinal region of the center line;
forming a potential cut line that halves the flap continuum along the center line;
forming flaps on the flap line by cutting the flap continuum in a direction orthogonal to the moving direction of the flap line;
transporting a front waistline member continuum or a rear waistline member continuum along a moving direction of a main body line; and
rotating the flaps that have been cut from the flap continuum by 90 degrees, and then placing the flaps, on the main body line, on the front waistline member continuum or on the rear waistline member continuum, so that the center line is orthogonal to the moving direction of the main body line,
wherein the moving direction of the flap line and the moving direction of the main body line face a same direction.

2. The method according to claim 1, further comprising:
cutting, on the main body line, the front waistline member continuum and the rear waistline member continuum by a predetermined interval length, along a direction orthogonal to the moving direction of the main body line,
wherein a width of each of the flaps in a direction orthogonal to the center line is shorter than the predetermined interval length.

3. The method according to claim 1, further comprising:
forming cut-out portions having a predetermined shape in a part of the vicinal region.

4. The method according to claim 1, further comprising:
on the flap line, folding side edge portions of the flap continuum toward the center line,
wherein in said placing the flaps, folded said edge portions of the flap continuum are bonded onto the front waistline member continuum or onto the rear waistline member continuum.

5. The method according to claim 1, further comprising:
placing the crotch members between the front waistline member continuum and the rear waistline member continuum so that the crotch members are apart from the other in the moving direction of the main body line,
wherein the front waistline member continuum and the rear waistline member continuum both have an elongated shape and are transported continuously on the main body line.

6. The method according to claim 2, wherein, in the cutting, the front waistline member continuum and the rear waistline member continuum are cut so that each width of the front waistline members in a width direction of the absorbent articles is equal to each width of the rear waistline members in a width direction of the absorbent articles.

7. An apparatus for manufacturing absorbent articles including a front waistline member, a rear waistline member, and a crotch member connecting the front waistline member and the rear waistline member, said apparatus comprising:
a latch member placing structure configured to place latch members on both sides of a vicinal region of a center line extending along a moving direction of a flap line, on an elongated flap continuum continuously transported on the flap line;
a potential cut line forming structure configured to form a potential cut line that halves the flap continuum along the center line; and
a cutting and placing structure configured to cut the flap continuum in a direction orthogonal to the moving direction of the flap line to obtain flaps, and to rotate the flaps cut from the flap continuum by 90 degrees, and then to place the flaps, on a main body line, on a front waistline member continuum or on a rear waistline member continuum, so that the center line is orthogonal to a moving direction of the main body line,
wherein the moving direction of the flap line and the moving direction of the main body line face a same direction.

8. The apparatus according to claim 7, further comprising a guiding roll configured to fold side edge portions of the flap continuum toward the center line on the flap line,
wherein said cutting and placing structure is further configured to place the folded said edge portions of the flap continuum onto the front waistline member continuum or onto the rear waistline member continuum.

9. The apparatus according to claim 7, wherein the cutting and placing structure comprises
a continuum cutting roll for cutting the flap continuum in the direction orthogonal to the moving direction of the flap line, and
a rotating drum for rotating the flaps that have been cut by the cutting roll.

* * * * *